(12) United States Patent
Dumas et al.

(10) Patent No.: US 10,413,502 B2
(45) Date of Patent: Sep. 17, 2019

(54) COSMETIC USE OF A PEPPERMINT EXTRACT

(71) Applicant: LVMH RECHERCHE, Saint-Jean de Braye (FR)

(72) Inventors: Marc Dumas, Saint Jean de Braye (FR); Olivier Jeanneton, Virty aux Loges (FR); Valentin Jeronimo-Monteiro, Trainou (FR); Carine Nizard, Ivry sur Seine (FR); Marielle Moreau, Marcq (FR)

(73) Assignee: LVMH RECHERCHE, Saint-Jean-de-Braye (FR)

( * ) Notice: Subject to any disclaimer, the term of this patent is extended or adjusted under 35 U.S.C. 154(b) by 73 days.

(21) Appl. No.: 15/548,681

(22) PCT Filed: Feb. 4, 2016

(86) PCT No.: PCT/FR2016/050238
§ 371 (c)(1),
(2) Date: Aug. 3, 2017

(87) PCT Pub. No.: WO2016/124862
PCT Pub. Date: Aug. 11, 2016

(65) Prior Publication Data
US 2018/0021248 A1    Jan. 25, 2018

(30) Foreign Application Priority Data
Feb. 4, 2015 (FR) .................... 15 50863

(51) Int. Cl.
| | | |
|---|---|---|
| A61K 36/00 | (2006.01) |
| A61K 8/9789 | (2017.01) |
| A61Q 19/00 | (2006.01) |
| A61Q 19/08 | (2006.01) |
| A61K 36/534 | (2006.01) |
| A61K 36/28 | (2006.01) |
| A61K 36/49 | (2006.01) |

(52) U.S. Cl.
CPC ............ A61K 8/9789 (2017.08); A61K 36/28 (2013.01); A61K 36/49 (2013.01); A61K 36/534 (2013.01); A61Q 19/00 (2013.01); A61Q 19/007 (2013.01); A61Q 19/08 (2013.01)

(58) Field of Classification Search
CPC .................................................. A61K 36/00
See application file for complete search history.

(56) References Cited

U.S. PATENT DOCUMENTS 2,463,264 A    3/1949  Graenacher et al.

FOREIGN PATENT DOCUMENTS

| EP | 669323 | 6/2012 |
|---|---|---|
| FR | 2848851 | 6/2004 |
| FR | 2895678 | 7/2007 |
| FR | 2962648 | 1/2012 |
| FR | 2978043 | 1/2013 |
| JP | 2001348337 A * | 12/2001 |
| JP | 2006176436 | 7/2006 |
| JP | 2007277149 | 10/2007 |
| JP | 2012236801 | 12/2012 |

OTHER PUBLICATIONS

Ahmadi, Evaluation the effectiveness of *Mentha piperita* (Peppermint) extract on release of Interleukin 8 in patients withi Inflammatory acne vulgaris. JDDG—Journal of the German Society of Dermatology, (Jun. 2014) vol. 12, Supp. Suppl. 2, pp. 12-13. (Year: 2014).*

Aithal et al.: "Role of Notch signalling pathway in cancer and its association with DNA methylation"; Department of Biotechnology, Journal of Genetics, 2013, vol. 92, pp. 667-675.

Bodo C. Melnik: "The Potential Role of Impaired Notch Signalling in Atopic Dermatitis"; Acta Dermato-Venereologica, 2014, pp. 1-9.

Seleit et al.: "Immunohistochemical expression of aberrant Notch-1 signaling in vitiligo: an implication for pathogenesis."; Ann, Diagn. Pathol., 2014, vol. 18, 1 page, abstract only.

Nowell et al.: "Cutaneous Notch signaling in health and disease." Cold Spring Hard Perspect Med, 2013, vol. 3, pp. 1-15.

Bielefeld et al.: "Cutaneous wound healing: recruiting developmental pathways for regeneration", Cell. Mol. Life Sci., 2013, vol. 70, pp. 2059-2081.

Palazzo et al.:"Role of neurotrophins on dermal fibroblast survival and differentiation"; Journal of Cellular Physiology, 2011, 29 pages.

Marconi et al.: "Expression and Function of Neurotrophins and Their Receptors in Human Keratinocytes", The Society of Investigative Dermatology, 2003, pp. 1515.

Provost et al.: "Ultraviolet A radiation transiently disrupts gap junctional communication in human keratinocytes", Am. J. Physiol, 2002, vol. 284, pp. C51-C59.

Barrandon et al.: "Three clonal types of keratinocyte with different capacities for multiplication" ; Proc. Natl. Acad. Sci., 1987, vol. 84, pp. 2302-2306.

(Continued)

*Primary Examiner* — Qiuwen Mi
(74) *Attorney, Agent, or Firm* — Hamre, Schumann, Mueller & Larson, P.C.

(57) ABSTRACT

The present invention relates to the use, in a cosmetic composition, of a peppermint extract, as agent intended to increase renewal of the cells of the epidermis associated with a deficiency in the expression of NOTCH proteins in keratinocyte progenitor cells, in particular for mature skin and/or skin exhibiting signs of dryness and of loss of firmness. The invention also relates to a cosmetic care method, for maintaining or regulating renewal of the cells of the epidermis associated with a deficiency in the expression of NOTCH proteins in keratinocyte progenitor cells, intended for mature and/or dry skin.

5 Claims, 1 Drawing Sheet

(56) References Cited

OTHER PUBLICATIONS

International Search Report issued in International Application No. PCT/FR2016/050238 dated May 3, 2016 (7 pages; English translation).

Written Opinion issued in International Application No. PCT/FR2016/050238 dated May 3, 2016 (7 pages).

* cited by examiner

COSMETIC USE OF A PEPPERMINT EXTRACT

The invention relates to the use of a peppermint (*Mentha piperita*) extract in cosmetic compositions, for maintaining or regulating renewal of the cells of the epidermis associated with a deficiency in the expression of NOTCH proteins in keratinocyte progenitor cells, in particular for mature skin and skin exhibiting signs of dryness.

PRIOR ART

The use of peppermint extract in cosmetic compositions has been known for a long time.

For example, an extract of *Mentha piperita* was proposed as active agent having a soothing effect for the skin in document FR 2848851.

Document FR 2895678 discloses the use of extracts from cells of at least one plant of the mint family as active agents in a cosmetic composition for treating skin disorders associated with excess melanogenesis and/or for preventing and/or reducing the synthesis and/or the release of melanin, and also the properties of said extracts with regard to the process of melanogenesis, especially induced by internal stress, for example emotional stress.

However, none of these documents discloses the action of a peppermint extract in maintaining or regulating renewal of the cells of the epidermis, in particular renewal of keratinocytes with a high clonogenic potential.

Indeed, it has entirely unexpectedly been discovered by the inventors of the present invention that a peppermint extract stimulates expression of the NOTCH protein which is present in human keratinocytes having such a potential.

Among the keratinocytes forming the epidermis, cells with a high clonogenic potential are distinguished, which cells will produce the largest amount of daughter cells and thereby play an essential role in the cell renewal of the epidermis, and in particular maintain this renewal over the long term.

These specific keratinocytes which will also be referred to as "stem cells" or "keratinocyte stem cells" or "keratinocyte progenitor cells" in the present application, represent less than 1% of the number of cells constituting the epidermis and are preferentially located in the basal layer thereof, which more effectively protects them from DNA damage, especially induced by the action of solar radiation, in particular UV-B rays which are largely filtered by the upper cell strata of the epidermis.

What are referred to as transit-amplifying cells, daughters of the above cells, have a lower regeneration potential than that of the "stem cells" defined above, but also participate in regeneration of the epidermis which avoids the stem cells being made to divide too frequently.

NOTCH proteins, such as NOTCH 1 and NOTCH 2 proteins, belong to a family of transmembrane receptors, which are activated by direct binding between the receptor and its ligands, borne by neighboring cells. This binding causes the release of an intracellular part of the receptor (NICD) from the cell membrane after cleavage by gamma secretase. The NICD fragment then migrates to the nucleus of the keratinocytes where it will associate with transcription factors to regulate a set of target genes (Aithal M. G. S et al *J. Genet.* (2013) *Role of NOTCH signaling pathway in cancer and its association with DNA methylation*).

In the epidermis, NOTCH plays an essential role by ensuring that cell proliferation and differentiation are coordinated to promote homeostasis of this tissue. Dysfunctions in the NOTCH signaling process leads to major anomalies for the epidermis and its appendages, causing functional losses, such as, for example, a defective cutaneous barrier or insufficient sebaceous production by reducing the number of sebocytes, which are the cells which produce sebum (Melnik B C *Acta Derm Venereol.* (2014), *The Potential Role of Impaired NOTCH Signalling in Atopic Dermatitis*). Several disorders also result from dysfunction of the NOTCH signaling process; atopy (Melnik B C, *Acta Derm Venereol.* (2014), *The Potential Role of Impaired NOTCH Signalling in Atopic Dermatitis*), vitiligo, with the loss of active epidermal or follicular melanocytes (Seleit I et al *Ann Diagn Pathol.* 2014 *Immunohistochemical expression of aberrant NOTCH-1 signaling in vitiligo: an implication for pathogenesis*), and also some cancers (Nowell C, *Cold Spring Harb Perspect Med.* (2013) *Cutaneous NOTCH signaling in health and disease*/Aithal M. G. S et al *J. Genet.* (2013) *Role of NOTCH signalling pathway in cancer and its association with DNA methylation*). Thus, NOTCH dysfunction may alone be the source of numerous cutaneous disturbances, whether regarding sebum production, the barrier function of the skin, or pigmentation.

Several studies are convergent in indicating that cell signaling controlled by NOTCH is essential for good skin repair and that it is reportedly involved in the regulation of several phases of the wound healing process, in particular in regulating angiogenesis, in the production of the extracellular matrix and in inflammation (Lirsten A *Cell. Mol. Life Sci.* (2013) *Cutaneous wound healing: recruiting developmental pathways for regeneration*).

It has been shown that NOTCH expression decreases in mature skin both in NOTCH and in vitro, in keratinocyte stem cells and their daughter cells, referred to as transit-amplifying cells, originating from aged individuals. (Palazzo E et al. *J Invest Dermatol* (2011), 131, S116-S117. *NOTCH-1 and NOTCH-2 modulate keratinocyte stem cell viability and differentiation during skin ageing and UVB exposure*).

Inactivation of NOTCH signaling blocks the cell cycle and prevents cell mitosis, and thus the process of regeneration of the epidermis. This inactivation of NOTCH also causes premature differentiation of the keratinocyte stem cells, with the consequence of depletion of the regenerative keratinocyte pool. Conversely, increasing NOTCH expression educes the process of differentiation of the keratinocytes (Morandi P et al. *J Invest Dermatol* (2014) *S2 NOTCH1 downregulates human keratinocyte differentiation: a feedback loop with suivivin*). These studies show that this protein plays a decisive role in maintaining undifferentiated keratinocyte populations, which are progenitors ensuring renewal of the epidermis. Thus, demonstrating the disappearance of NOTCH expression in the epidermis with increasing age and during exposure to UVB radiation may be considered as one of the biological causes of the loss of cutaneous cell regeneration during aging and photoaging.

The inventors have now shown that it is possible to significantly stimulate the expression of the NOTCH protein in the keratinocytes of the epidermis, and more precisely in keratinocytes having the ability to divide, also referred to as keratinocyte progenitor cells.

Due to its stimulating action on NOTCH production in keratinocyte progenitor cells, peppermint extract is a particularly beneficial agent for maintaining or reinforcing the renewal of cells of the epidermis.

It is also particularly possible to make use of the novel properties of this peppermint extract in the case in which the epidermis has a disordered regenerative process.

This is most particularly the case, on the one hand, for mature skin which has a reduced regeneration capacity, and on the other hand, for dehydrated skin, since dehydration may adversely affect the regenerative process thereof.

Indeed, the inventors have observed that a hyperosmotic environment causing a loss of cell water reduces the capacity of keratinocyte progenitor cells to produce daughter cells. Thus, exposure of the cutaneous cells to dehydration significantly reduces their regeneration capacity.

In support of this observation is the fact that the proliferation of cells of the epidermis and skin wound healing are slowed when there is a deficit in aquaporin 3, a water channel which, by facilitating the supply and distribution of cutaneous water, makes it possible to ensure the water balance of the epidermis (M Boury-Jamot, et al. *Skin Aquaporins: Function in Hydration, Wound Healing, and Skin Epidermis Homeostasis*. E Beitz (ed.), *Aquaporins, Handbook of Experimental Pharmacology* 190, 205c Springer-Verlag Berlin Heidelberg (2009) 205-214.

Moreover, due to exposure of the skin to drying environmental conditions, the cells of the epidermis may be confronted with situations of dehydration. Exposure of the skin to cold or to successive cleaning operations may disrupt the lipids of the cutaneous barrier which enable water to remain in the skin, and thereby accentuate water loss, by which process the cutaneous cells will be locally exposed to a deficit of water. Other stressing environmental factors such as exposure to oxidizing atmospheric pollutants (ozone) or to solar radiation, may also adversely affect the water barrier. Thus, the epidermis may frequently be in situations of exposure which are liable to lead to the dehydration thereof.

The inventors have also observed that by partially removing the cutaneous barrier with adhesive strips so as to double the cutaneous water loss (referred to as "insensible water loss" or "IWL"), the process of reconstructing this barrier (returning to the initial IWL), was much slower when the skin was dry. Thus, skin dryness increases the duration of exposure to dehydration when the cutaneous barrier is damaged.

The present invention thus proposes a method making it possible to maintain or regulate renewal of the cells of the epidermis associated with a deficiency in the expression of NOTCH proteins in keratinocyte progenitor cells, in dry and dehydrated skin and/or mature skin.

Another aspect of the invention relates to the capacity of the keratinocyte stem cells of the epidermis to secrete more of the neurotrophin NGF (nerve growth factor) than other keratinocytes (Marconi A et al. *J Invest Dermatol* (2003) 121, 1515-1521; *Expression and Function of Neurotrophins and Their Receptors in Cultured Human Keratinocytes*). It has been shown that NGF was capable of stimulating tensioning of type I collagen, which is predominant in the dermis, via dermal fibroblasts (Palazzo E et al. *J Cell Physiol.* (2012) 227:1017-23; *Role of neurotrophins on dermal fibroblast survival and differentiation*).

Thus, the present invention also aims to contribute to the process of firmness and elasticity of the dermis, by maintaining the status of keratinocyte stem cells closely linked to the strong expression of the NOTCH protein.

Finally, the authors have demonstrated, unexpectedly, a strong link between NOTCH and the intracellular communication junctions referred to as gap junctions. These communication junctions enable adjacent keratinocytes to exchange the small molecules they contain with one another, in order to synchronize. These junctions are involved in the regulation and homeostasis of the epidermis and are strongly adversely affected by UVA radiation, which is a major contributor to skin photoaging (Provost N et al. *Am J Physiol Cell Physiol* 284: C51059, 2003 *Ultraviolet A radiation transiently disrupts gap junctional communication in human keratinocytes*).

The authors have observed that by blocking the signals emitted by the NOTCH protein, by inhibiting gamma secretase which is the perpetrator thereof, exchanges between keratinocytes which occur via gap junctions and are measured by following the transfer of the dye lucifer yellow were greatly reduced. The authors also measured the fact that the peppermint extract stimulates the diffusion of this dye between the keratinocytes but that this stimulation did not occur when the signals sent by NOTCH were blocked by the gamma secretase inhibitor DAPT (N—[N-(3,5-difluorophenacetyl)-L-alanyl]-S-phenylglycine t-butyl ester). They also show that, aside from the stimulating action of the peppermint extract on intracellular exchanges via gap junctions, stimulation also occurs via that of NOTCH and its signals.

Thus, the present invention proposes a treatment method intended to resynchronize keratinocyte progenitor cells, in particular to combat photoaging induced by UVA radiation.

The unexpected demonstration of the activity of peppermint extract with regard to the stimulation of the production of the NOTCH protein is particularly advantageous because the expression of NOTCH in cutaneous stem cells decreases with age, which clearly justifies the use of peppermint extract in cosmetic compositions for skin care in which it is sought to maintain or stimulate the renewal of the cells of the epidermis.

AIMS OF THE INVENTION

Thus, the main purpose of the present invention is to provide a novel use for a peppermint extract.

Another purpose of the present invention is to provide a cosmetic care method intended for maintaining or regulating renewal of the cells of the epidermis associated with a deficiency in the expression of NOTCH proteins in keratinocyte progenitor cells.

The present invention is also particularly suited to skins which have a deficit of NOTCH production, skins referred to as mature, in particular in areas of the face, of the décolletage, and of the hands which are heavily exposed to the sun, and also in areas of the body in which dryness, is more intense, for example the legs, the arms, and the hands but also the contour of the eyes, the lips, and also in areas of the skin where the loss of firmness may be great, for example the jowls and the chin, the eyelids, the underarms, the thighs and the stomach.

Another purpose of the present invention is to provide a cosmetic care method intended for dry and/or mature and/or photoaged and/or dry and/or dehydrated skins and/or skins exhibiting signs of sagging.

The present invention may be used to accelerate repair of the cutaneous barrier and of the epidermis and healing of the surface layers of the skin.

SUMMARY OF THE INVENTION

The invention relates to the use, in a cosmetic composition, of a peppermint extract for maintaining or regulating renewal of the cells of the skin's epidermis associated with a deficiency in the expression of NOTCH proteins in keratinocyte progenitor cells, said composition also comprising a cosmetically acceptable excipient.

DETAILED DESCRIPTION OF THE INVENTION

The present invention relates to the use, in a cosmetic composition, of a peppermint extract as agent intended to maintain or regulate renewal of the cells of the epidermis, said composition also comprising a cosmetically acceptable excipient.

A first subject of the invention relates to a composition comprising an effective amount of peppermint extract, also referred to as *Mentha piperita*, for use thereof for increasing renewal of the cells of the skin's epidermis associated with a deficiency in the expression of NOTCH proteins in keratinocyte progenitor cells.

The cells are preferably keratinocytes located in the basal layer of the epidermis, chosen from the group consisting of transit-amplifying keratinocytes and keratinocytes with a high clonogenic potential also referred to as keratinocyte stem cells or keratinocyte progenitor cells.

Renewal of the keratinocytes is advantageously produced by stimulating the expression of NOTCH genes in the keratinocytes, the expression of NOTCH proteins in said keratinocytes being deficient.

Renewal of the keratinocytes is advantageously promoted by stimulating NOTCH gene expression in the keratinocytes, the stimulation being defined as corresponding to quantification of the gene expression (RQ) of the gene coding for the NOTCH 1 or NOTCH 2 proteins of greater than 1 and being significantly different thereto by a statistical test. The stimulation of NOTCH gene expression is preferably such that quantification of the gene expression (RQ corresponding to quantification of the NOTCH gene relative to an invariant gene used as reference) is significantly greater than or equal to a value chosen from the group consisting of 1.2; 1.3; 1.4; 1.5; 1.6; 1.7; 1.8 and 1.9. Quantification of the gene expression is preferably measured by quantitative real-time PCR (qRT-PCR) expressed relative to an untreated control.

The peppermint extract may be an extract prepared from any plant material originating from said plant, obtained by in vivo culture or in vitro culture by techniques for the laboratory culture of plant cells. In the latter mode for obtaining the extract, it is sought to artificially produce differentiated or undifferentiated plant cells from plant cells originating from at least one organ of the plant.

The plant material used may be the whole plant or a part of the plant such as the leaves, the stem, the flowers, the seeds or the roots.

The peppermint extract is preferably an extract of the aerial parts of the peppermint plant.

Before the extraction step, the plant material may have been dried and/or ground. An alternative consists in drying the unharvested plant and then recovering the part of interest.

The extract may be prepared by different extraction methods known to those skilled in the art.

According to the invention, the peppermint extract (*Mentha piperita*) is obtained by means of at least one polar solvent.

Within the context of the invention, "polar solvent" is intended to mean a liquid, the dipole moment of which is not zero, more particularly a compound comprising at least one covalent bond between two atoms, the difference in electronegativity, $\Delta En$, between which is greater than 0.4 and less than 1.7 ($0.4 < \Delta En < 1.7$) according to the Pauling scale.

The preferred polar solvents are those consisting of a compound comprising at least one polar covalent bond of O—H type. As particularly preferred polar solvent, a solvent or a mixture of solvents are chosen, selected from water, a C1-C4 alcohol, for example ethanol, a C2-C6 glycol, preferentially selected from glycerol, butylene glycol and propylene glycol, or else any mixture thereof.

According to a preferred embodiment, the finely pulverized plant material is dispersed in water, then enzymatic hydrolysis is carried out by adding enzymes into the water, with adjustment to the optimal pH for the enzyme.

According to a particular embodiment, the extract is an extract of the aerial parts, such as leaves, obtained by enzymatic hydrolysis in aqueous medium.

The extraction may be carried out under hot conditions by refluxing, or else by maceration at room temperature.

It is advantageously possible to use ultrasound during the extraction in order to improve the weight yield of said extraction.

The extraction process may also comprise at least one step of separating the solvent phase and the spent plant material by settling out, ultrafiltration or centrifugation, of decoloration and/or purification and/or delipidation, for example in the form of a treatment of the extract by a solution of at least one polar solvent in the presence of active charcoal particles and/or by a treatment of the extract by means of an apolar solvent which is acceptable from a cosmetic or dermatological perspective, especially an alkane comprising 6 or 7 carbon atoms or supercritical $CO_2$.

The extraction process may also be supplemented by a step for partial or total elimination of the extraction solvents, so as to concentrate the extract.

In the former case, the extract is generally concentrated until a concentrate devoid of a significant amount of organic solvents is obtained; in the latter case, a dry residue is obtained.

Alternatively, the product of the extraction step may be atomized and/or lyophilized in order to be present in the form of a powder.

The peppermint extract may be used in a cosmetic composition in the form of a powder or else in the form of a solution or a suspension of said powder in at least one cosmetically acceptable solvent, which may be identical to or different from that which served for the extraction.

By way of example of extract of use within the context of the present invention, it is possible to use an extract prepared by the method described in document FR 2848851.

It is also possible to use commercially available peppermint extracts. By way of example, mention will be made of an extract of peppermint leaves with propylene glycol, sold by Alban Muller, or an extract of peppermint leaves sold under the name CALMISKIN® by Silab.

Unless indicated otherwise, the amounts of mint extract are given as dry matter. "Dry matter" is used to denote the residual amount of material following desiccation of the extract, such as may be measured by any method known to those skilled in the art. The measurement may for example be carried out according to the protocol described in patent application FR 2848851.

The peppermint extract is present in an effective amount for maintaining or regulating the renewal of cells of the epidermis, and especially for effectively stimulating the production of NOTCH in the cells located in the basal layer of the epidermis, such as cells with a high clonogenic potential and/or transit-amplifying cells.

Thus, the cosmetic composition used within the context of the invention may comprise from 0.005 to 0.5% by weight of dry matter of the extract relative to the weight of the composition, advantageously between 0.02% and 0.2% by weight of dry matter relative to the total weight of the composition.

Aside from a peppermint extract as described above, the compositions according to the invention may comprise one or more other cosmetically acceptable active agents having similar and/or complementary cosmetic effects to the peppermint extract, excipients and/or formulation vehicle selected more particularly with regard to the method of administration considered for the composition.

It will be in particular possible to combine, with the peppermint extract, an active agent which acts on NOTCH expression in normal human keratinocytes, chosen from an aqueous extract of beech (*Fagus Sylvatica*) buds, for example that sold under the name Gatuline® RP by Gatefossé or else an aqueous extract of *Bellis perennis* flowers, for example that sold under the name Belides® by CLR.

It will be possible for the peppermint extract to advantageously be combined with an effective amount of extracts stimulating or promoting the formation of survivin, a protein which is strongly expressed in keratinocyte progenitor cells and which has a protective role with regard to cell apoptosis, such as, for example, *Coleus forskolii, Limnophila conferta* and *Lepechinia caulescens* extract or else an *Oryza sativa* extract such as Survixyl RZ™ from Ashland, stimulating a protein complex called CPC (chromosomal passenger complex) which contains survivin.

It will be in particular possible to combine, with the peppermint extract, one or more extracts from plants known to slow or prevent the appearance of signs of skin dryness by a humectant effect provided by small hydrophilic molecules, an action stimulating the formation of hyaluronic acid, such as with the *Alpinia galanga* leaf extract, or inhibiting the degradation thereof, an action stimulating the formation of the constituents of the tight junctions of the epidermis in order to limit the loss of intercellular water, such as with an *Ophiopogon japonicus* root extract, an action stimulating the formation of the hyaluronic acid receptor or CD44, such as with the *Viola tricolor* extract, an action stimulating the formation of the adherens, desmosome and corneodesmosome junctions of the epidermis, such as with the *Arolea lavanda* extract, an action stimulating the formation of epidermal lipids, in particular ceramides, fatty acids and cholesterol which contribute to the water barrier function, such as with a millet extract, an action stimulating the synthesis of sebum, in particular of squalene and of triglycerides, or conversely an action inhibiting 5-alpha-reductase such as the *Linum usitatissimum* seed extract, or else an action which partially occludes the surface of the skin, by a film-forming formulation.

The peppermint extract may also be combined with one or more molecules and/or one or more plant extracts having hydrating properties, such as glycols, in particular glycerol, or natural polyols, natural or synthetic ceramides, urea, hyaluronic acid or lactic acid.

It is particularly beneficial to combine the peppermint extract with an active agent or active agents which, used alone or in combination, increase the expression of aquaporins in skin cells, such as an *Ajuga turkestanica* extract, a *Paeonia suffrutica* extract, a rose, *kniphophia uvaria, Helianthus annuus, Oriza sativa, Malva sylvestris, Sanguisorba officinalis, Glycine max, Saccharomyces cerevisiae, Onopordum acanthrium, Zea mays, Filipendula ulmaria, Salix alba, Rhodophyccea*, or *Centella asiatica* extract, and ascorbic acid 2-glucoside.

The peppermint extract may also advantageously be combined, in cosmetic compositions, with at least one extract from one or more plants belonging to the orchid family (Orchidaceae), in particular an extract of at least one orchid of the *Vanda* genus, such as the orchid *Vanda coerulea*, which has an action on aquaporins of the cells of the epidermis, or *Dendrobium*, or else *Phalaenopsis*.

It may also be particularly beneficial to combine, with the peppermint extract, one or more molecules or plant extracts having antioxidant properties, such as, for example, polyphenols, tannic acid, epigallocatechin and natural extracts containing same, epigallocatechin-3-gallate, anthocyanins, carotenes, rosemary extracts, olive tree leaf extracts, green tea, resveratrol and derivatives thereof, pycnogenol, ergothioneine, N-acetylcysteine, biotin, chelators, idebenone, plant extracts such as Pronalen Bioprotect™ from Provital, co-enzyme Q10, bioflavonoids, SODs (superoxide dismutases), phytantriol, lignans, melatonin, pidolates, a tocopherol ester or a salt thereof, ascorbic acid and the salts thereof, arginine pyrrolidone carboxylate, selenium-based derivatives, glutathione, and the various isoforms of tocotrienol and vitamin E, including vitamin E phosphate and ergothioneine.

The peppermint extract may advantageously be combined with chemical or physical screening agents against UVA and UVB type solar radiation, such as synthetic screening agents combined, or not combined, with screening agents consisting of particles capable of alleviating the effects of this radiation on the skin, and/or particles capable of reflecting sunlight.

The UV screening agent may be chosen from inorganic UV screening agents, organic hydrophilic UV screening agents and organic liposoluble UV screening agents.

"Organic hydrophilic UV screening agent" is intended to mean any organic compound absorbing ultraviolet (UV) radiation in the range of wavelengths extending from 280 nm to 400 nm, which may be dissolved in the aqueous phase of the composition, or which may be dispersed therein in colloidal form or in micellar form.

"Organic liposoluble UV screening agent" is intended to mean any organic compound absorbing UV radiation in the range of wavelengths extending from 280 nm to 400 nm, which may be dissolved, in the molecular state, in an oil, or be dispersed in an oil in colloidal form or in micellar form.

The composition of the invention advantageously comprises at least one inorganic UV screening agent chosen from metal oxide pigments.

These pigments are advantageously oxides of titanium (amorphous or crystallized in rutile and/or anatase form), of iron, of zinc, of zirconium or of cerium.

The metal oxide pigment particles generally have a mean size (D50) of between 5 nm and 100 nm, preferably between 10 nm and 50 nm.

The pigments may have been surface-treated, that is to say have undergone one or more surface treatments of chemical, electronic, mechanochemical and/or mechanical nature with compounds such as silicon oxides, metal oxides such as cerium oxide, alumina, silica, aluminum compounds, silicon compounds, or mixtures thereof, amino acids, beeswax, fatty acids, fatty alcohols, anionic surfactants, lecithins, sodium, potassium, zinc, iron or aluminum salts of fatty acids, metal alkoxides (of titanium or aluminum), polyethylene, silicones chosen from the group containing alkyl silanes, polydialkylsiloxanes and polyalkylhydrosiloxanes, proteins (collagen, elastin), alkanolamines or sodium hexametaphosphate.

Among the hydrophilic UV screening agents, use may be made of the following UV screening agents, designated below by their INCI name or their chemical name:

terephthalylidene dicamphor sulfonic acid (INCI name: Terephthalylidene Dicamphor Sulfonic Acid) sold under the name MEXORYL® SX by CHIMEX, bis-benzoazolyl derivatives such as those described in patents EP 669 323 and U.S. Pat. No. 2,463,264 and more particularly the compound Disodium Phenyl Dibenzimidazole Tetrasulfonate sold under the trade name NEO HELIOPAN® AP by Haarmann & Reimer, p-aminobenzoic acid (INCI name: PABA) and derivatives thereof, such as 1-(4-aminobenzoate)-1,2,3-propanetriol (INCI name: Glyceryl PABA) and PEG-25 PABA sold under the name UVINUL® P25 by BASF, 2-phenylbenzimidazole-5-sulfonic add (INCI name: Phenylbenzimidazole Sulfonic Acid), especially sold under the trade name EUSOLEX® 232 by MERCK, triethanolamine salicylate, 3-(4'-sulfobenzylidene) camphor (INCI name: Benzylidene camphor sulfonic acid) sold under the name MEXORYL® SL by CHIMEX, Methylene bis-Benzotriazolyl Tetramethylbutylphenol (USAN name: BISOCTRIZOLE), sold under the reference Tinosorb® M, or MIXXIM® BB/100 by FAIRMOUNT CHEMICAL;

3-(4'-trimethylammonium benzylidene)-1-bornan-2-one methyl sulfate (INCI name: Camphor Benzalkonium Methosulfate) sold under the name "MEXORYL SO" by CHIMEX, Benzophenone-4 sold under the trade name UVINUL® MS40.

It is also possible to use, as organic hydrophilic UV screening agent, organic molecules which screen UV rays and which are lipophilic in nature (dissolved or dispersed in a non-aqueous liquid), which have been made hydrophilic by adsorption onto a hydrophilic support of small particle size, such as polymer particles. Mention may be made, for example, of bis-ethylhexyloxyphenol methoxyphenyl triazine, which is a lipophilic UV screening agent adsorbed onto particles of polymethyl methacrylate (PMMA). The organic hydrophilic UV screening agent may thus be an organic lipophilic molecule which screens UV rays, adsorbed or absorbed on a hydrophilic support which cannot screen UV rays, such as an organic polymer.

The organic liposoluble UV screening agents may especially be chosen from different families of chemical compounds. Mention may especially be made of the derivatives of para-aminobenzoic acid, salicylic derivatives, cinnamic derivatives, aminobenzophenones, anthranilic derivatives, dibenzoylmethane derivatives, [beta],[beta]'-diphenylacrylate derivatives, benzylidene camphor derivatives, phenyl benzotriazole derivatives, triazine derivatives, bis(resorcinyl)triazines, imidazoline derivatives, benzalmalonate derivatives, 4,4-diarylbutaliene derivatives, benzoxazole derivatives, merocyanins and mixtures thereof.

The content of UV screening agent in the composition advantageously varies from 0.5 to 40% by weight, preferably from 5 to 30% by weight, and even more preferentially from 10 to 20% by weight relative to the total weight of the composition.

The compositions may be present in any of the galenical forms normally used depending on the preferred method of application or administration. These compositions are prepared according to the usual methods.

In a known way, the compositions may contain adjuvants which are customary in the cosmetics field, such as fatty substances, emulsifiers, hydrophilic or lipophilic gelling agents, hydrophilic or lipophilic active agents, preservatives, antioxidants, fragrances, fillers and dyestuffs.

The compositions are preferably formulated for application to the skin. They have a particularly sought-after effect for maintaining or regulating renewal of the cells of the epidermis associated with a deficiency in the expression of NOTCH proteins in keratinocyte progenitor cells, when said composition is applied to the skin of the face or of the body.

The compositions are particularly formulated to be suitable for skins exhibiting signs of dryness, or for mature and/or dry skins. The present invention is particularly suited to skins having a disordered regenerative process—for example a deficit of NOTCH production—such as what are referred to as dry or mature skins.

The compositions are applied to the skin, in particular to areas of the face, and more particularly of the contour of the eye, of the décolletage, and of the hands which are heavily exposed to the sun, and also in areas of the body in which dryness is more intense, for example the legs, the arms, and the hands but also the lips, and also in areas of the skin where the loss of firmness may be great, for example the jowls and the chin, the eyelids, the underarms, the thighs and the stomach.

The cosmetic composition may for example be in the form of aqueous, aqueous-alcoholic or oily solutions, of dispersions of solution type or dispersions of lotion or serum type, of oil-in-water or water-in-oil emulsions or emulsions comprising a glycerol-based or silicone-based phase, of liquid or semi-liquid consistency of milk type, of suspensions or emulsions of cream type, of aqueous (hydrogels) or anhydrous gels, of microemulsions, of microcapsules or microparticles dispersed in a continuous liquid or semi-liquid phase, or of vesicular dispersions of ionic and/or non-ionic type.

The compositions may be present, for example, in the form of care creams, care gels, masks, makeup products such as mascaras or lipsticks, or makeup removers, or else in the form of a mask, a stick, or else a patch.

When the composition is an emulsion, it comprises a fatty phase comprising oils, and also emulsifiers and co-emulsifiers chosen from those conventionally used in the cosmetics field.

Among the oils of use in cosmetics, mention may be made of mineral oils such as hydrogenated polyisobutene and liquid petroleum jelly, plant oils derived from shea butter, sunflower or else apricot kernels, animal oils, synthetic oils, especially Purcellin oil, isopropyl myristate and ethylhexyl palmitate, and fluoro oils such as, for example, perfluoropolyethers. It is also possible to use fatty alcohols, fatty acids such as, for example, stearic acid, waxes, especially paraffin, carnauba or beeswax. It is also possible to use silicone oils, and for example cyclomethicones and dimethicones, and silicone waxes, resins and gums.

As emulsifiers, mention may be made for example of glyceryl stearate, polysorbate 60, PPG-3 myristyl ether, silicone emulsifiers such as cetyl dimethicone copolyol and sorbitan mono- or tristearate, PEG-40 stearate, or oxyethylenated sorbitan monostearate (20EO).

As hydrophilic gelling agents, mention may be made of carboxylic polymers, acrylic copolymers, polyacrylamides, polysaccharides such as cellulose-based derivatives, natural gums and days.

As lipophilic gelling agents, mention may be made of modified days such as bentones, metal salts of fatty acids such as aluminum stearates and hydrophobic silica, or else ethyl cellulose and polyethylene.

Depending on their nature, these excipients are introduced into the fatty phase, into the aqueous phase and/or into the lipid vesicles.

As described above, the present invention relates to a use of a peppermint extract, as cosmetic agent intended to maintain or regulate renewal of the cells of the skin's epidermis associated with a deficiency in the expression of NOTCH proteins in keratinocyte progenitor cells, in particular for mature and/or dry skin. "Mature skin" is intended to mean the skin of a person more than 35 years old, more than 40 years old, or even more than 45 years old.

Another subject of the invention is a cosmetic care method using the peppermint extract defined above or a cosmetic composition as defined above comprising an effective amount of said extract for maintaining or regulating renewal of the cells of the skin's epidermis associated with a deficiency in the expression of NOTCH proteins in keratinocyte progenitor cells.

Yet another subject of the invention is a method for the cosmetic care of the skin, for maintaining or regulating renewal of the cells of the skin's epidermis associated with a deficiency in the expression of NOTCH proteins in keratinocyte progenitor cells, which comprises the application, to at least a portion of the face or the body exhibiting signs of skin aging, photoaging, sagging or dryness caused by a disordered regenerative process of the skin, of an effective amount of a peppermint extract.

Another subject of the invention is a method for the cosmetic care of mature skins or skins exhibiting signs of dryness, which comprises the application, to at least a portion of the face or the body, of an effective amount of peppermint extract as described above, or else of a composition containing said extract and as defined above.

The cosmetic method of the invention may be carried out by topical application, daily or several times a day, of the composition described above.

The characteristics which have been described in relation to the first subject of the invention, relating to the use of a peppermint extract for maintaining or regulating renewal of the epidermis, apply to the characteristics of the method of the invention, which constitutes a second subject of the invention.

As emerges dearly from the following examples, the applicant has demonstrated the benefit of a peppermint extract for stimulating the expression of the NOTCH protein, in particular in cells with a high clonogenic potential or stem cells.

Other purposes, characteristics and advantages of the invention will become clear in light of the following explanatory description given with reference to examples of tests demonstrating the abovementioned properties for the peppermint extract, and examples of cosmetic compositions using this agent, given merely by way of illustration.

In the examples, all percentages are given by weight, the temperature is in degrees celsius and the pressure is atmospheric pressure, unless indicated otherwise.

Example 1: Evaluation of the Effects of a Peppermint Extract on the Expression of Genes Coding for the NOTCH Protein The study was carried out using keratinocyte clones according to the method developed by Barrandon and Green (Barrandon Y and Green H.; *Proc Natl Acad Sci USA* 1987, 84: 2302-2306) which makes it possible to analyze and distinguish keratinocytes having a high capacity for forming clones (also referred to as "keratinocyte stem cells" or "stem cells" or "progenitor cells") or having intermediate or low capacity (daughter cells referred to as transit-amplifying cells).

The aim of this study was to evaluate the effect of the peppermint extract on stem cells in culture.

Several extracts, including CALMISKIN®, were tested at the doses reported in the following table. The doses are expressed as percentage by weight of the commercial solution in the cell culture medium.

| Product name | Doses tested |
| --- | --- |
| Calmiskin GR ® | 1.5%; 0.75%; 0.375%; 0.18%; 0.09% |
| Gatuline RP ® | 5%; 2.5%; 1.25%; 0.625% |
| Belides ® | 0.625%; 0.312%; 0.156%; 0.078% |

I. Treatment of NHK Cells

Normal Human Keratinocytes (NHKs) are used, originating from an abdominoplasty from a female donor of 26 years of age.

The cells were provided at confluence in Epilife medium containing P6, with a seeding density of 125 000 cells per well, in 12-well plates. The cells are then treated with the different active ingredients prepared extemporaneously at the final usage concentrations in Epilife medium not containing any supplement. After 24 hours of treatment, the cells are recovered in order to extract the total RNAs therefrom.

II. Real-Time Quantitative PCR (RT-qPCR)

II.1 Obtaining the Total RNAs by Means of MicroLab-STAR (HAMILTON)

The cell culture medium is eliminated and 250 µl of lysis buffer RLT (supplied in the Nucleospin RNA kit, Ref. 740709.4, Macherey-Nagel) are added. The cells are scraped by means of a cell scraper, then the cell lysate is recovered in a 1.2 ml deepwell plate (supplied in the Nucleospin RNA kit). The total RNAs are then extracted. The solutions of total RNAs obtained are assayed by means of a microplate reader, spectrostarNANO (BMG Labtech), coupled to MicrolabSTAR.

This apparatus is connected to the computer running the robot platform, and has the specific software for analyzing the results. The technique requires a 384-well microplate (384 µclear plate black LoBase ref:788876, Greiner), a positive control (RNA 250 ref: AM7155 Applied) making it possible to check the pipetting operations performed by the robot and also the values generated by the spectrostarNANO reader.

II.2 Synthesis of the Complementary DNAs

The reverse transcription (RT) kit used is the High Capacity Reverse Transcription Kit (Ref. 4368813, Life Technologies-Applied), used according to the supplied protocol. 500 ng of total RNAs are diluted in water to give a final volume of 25 µl. They are then incubated for 10 minutes at 25° C. then 2 hours at 37° C. in the presence of 25 µl of High Capacity Reverse Transcription. Kit 2× reaction mixture, prepared beforehand as indicated below. The different operations are carried out by the MicrolabSTAR platform and the different incubations are carried out within the TRobot (Biométra).

The High Capacity Reverse Transcription Kit 2× reaction mixture for one reaction has the following composition:

| Reagents | volume |
|---|---|
| RT buffer | 5 µl |
| dNTP buffer | 2 µl |
| Random primer | 5 µl |
| RNaseOUT | 0.5 µl |
| RT | 2.5 µl |
| H2O | 10 µl |

II.3 Real-Time Quantitative PCR

The effect of the treatments is evaluated by real-time quantitative PCR with the fast 96-well block of the 7900HT and the reagents from Life Technologies-Applied. The TaqMan gene expression assay primers used are:
Housekeeping gene: beta-2-microglobulin (β2M): Hs99999907_m1
NOTCH 1 target gene: Hs00413187
NOTCH 2 target gene: Hs00225747
Reaction mixture for one reaction:
TaqMan Fast universal PCR master mix (2×) (Ref 4 . . . 62043, 10 µl)
TaqMan gene expression assay 20× (Hs00000000_m1), 1 µl
H2O, 4 µl The 15 µl of the mixture are placed in the wells of a 96-well plate specially designed for the 7900HT apparatus (ref 4346906); 5 µl of water are added (for the blank) or 5 µl of successive dilutions of cDNA (for the range) or 5 µl of samples in the corresponding wells. All the steps are carried out by the MicrolabSTAR.

II.4. Analysis of the Results

Real-time quantitative PCR may be made use of if its efficiency is between 90% and 110%. This efficiency is evaluated by setting up a standard range from a series of dilutions of cDNA extracted from the appropriate cells. The value of the slope obtained reflects the amplification efficiency; a PCR is 100% effective when the 2n rule (n=number of cycles, namely 40) is met and the value of the slope is −3.32. For each sample, the number of cycles at which the signal appears is determined by the SDS 2.3 software; by virtue of the calibration straight line established with the standard range, the concentration in terms of transcript copy number may thus be calculated. For the same assay, the levels of expression of the transcripts of interest are standardized relative to the value obtained for the housekeeping gene beta-2-microglobulin. This gene, the expression of which is constitutive and invariant, makes it possible to overcome any variations in amounts between assays, especially due to differing efficiencies of the reverse transcription step. Quantification of the transcriptional activity is determined by the difference in a Ct (Cycle threshold) of the target gene and of the housekeeping gene. This is relative quantification, which is obtained by the following calculation, in which untreated is equal to 1.

$RQ=2-\Delta\Delta Ct=2-$(treated target gene+$Ct$ untreated target gene)/2−($Ct$ treated housekeeping gene−untreated housekeeping gene)

In order to evaluate statistically significant variations in transcriptional activity, the Student's t-test was used. Each condition is carried out in triplicate (3 untreated and 3 treated, under the same conditions). Fisher's F-test is firstly applied by comparing the two data matrices. Significant transcriptional variations will be those which have a Student's t-test value of less than alpha=0.05. The data presented in the results section are the ratios of the amounts obtained in the treated samples versus the untreated samples, everything relative to the housekeeping gene beta-2-microglobulin.

The Student's statistical test was used to compare the active ingredient as a function of its solvent control. The results were considered to be significant for $p<0.05$ (*).

Results

Stimulation of NOTCH gene expression is observed for the CALMISKIN® peppermint extract solution.

Figure 1:
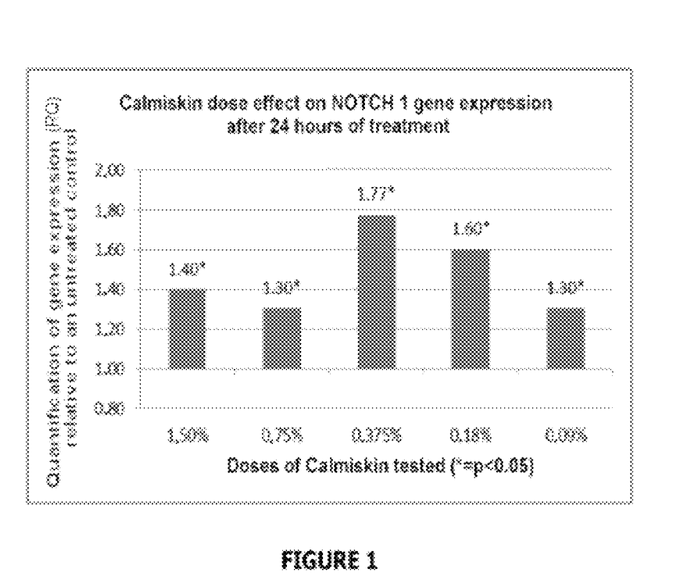
FIG. 1, given with reference to example 1, presents in histogram form the expression of NOTCH 1 in keratinocyte progenitor cells in culture exposed to a peppermint extract.
Figure 2:
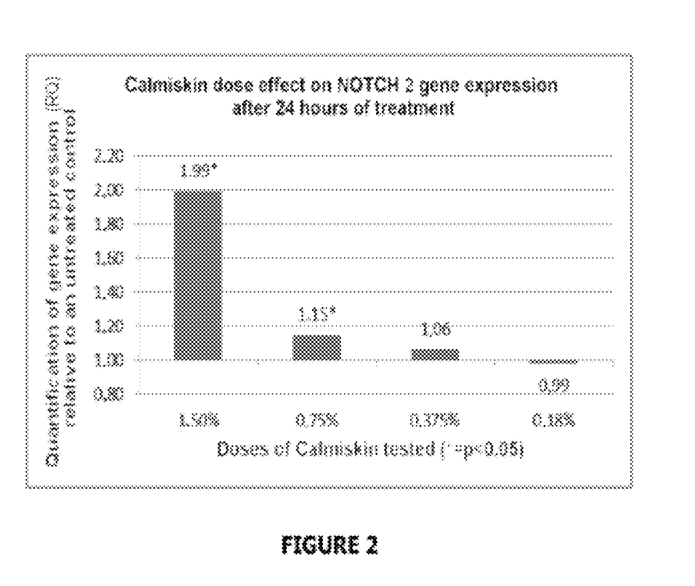
FIG. 2, also given with reference to example 1, presents in histogram form the expression of NOTCH 2 in keratinocyte progenitor cells in culture exposed to a peppermint extract.

The results are presented in FIGS. 1 and 2.

It is noted that the NOTCH 1 gene responds to lower concentrations of extract than NOTCH 2.

Conclusions

The peppermint extract stimulates NOTCH 1 and NOTCH 2 gene expression.

The results show that a peppermint extract stimulates NOTCH 1 protein expression in the concentration range from 0.09% to 1.5% but also NOTCH 2 in the concentration range from 0.375% to 1.5%, such that this extract is effective on several representatives of the NOTCH protein family.

Example 2—Cosmetic Compositions

The peppermint extract is used as active agent for maintaining or regulating renewal of cells of the epidermis in the following cosmetic compositions.

1—Lotion

An aqueous solution comprising the following active agents is prepared (percentage by weight):

|  | % |
|---|---|
| Calmiskin ® | 2 |
| Glycerol | 3.0 |
| *Malva sylvestris* extract | 0.2 |
| *Centella asiatica* heterosides | 0.02 |
| High and low molecular weight hyaluronic acids | 0.05 |
| Excipients | q.s. |

Calmiskin® is a solution of peppermint extract, sold by Silab, prepared from the aerial parts of the plant.

The lotion is applied daily to the face.

2—Moisturizing Day Cream

A moisturizing emulsion is prepared, the formulation of which is indicated below (% by weight):

|  | % |
|---|---|
| Phase A | |
| Calmiskin ® | 0.75 |
| 1% solution of *Vanda coerulea* extract | 0.3 |
| Phenoxyethanol | 0.5 |
| Xanthan gum | 0.2 |
| Acrylates/C20-30 alkyl acrylate crosspolymers | 0.15 |
| Tetrasodium EDTA | 0.1 |
| Water | q.s. |
| Phase B | |
| Hydrogenated polyisobutene | 4 |
| Squalane | 3 |
| Caprylic/capric triglyceride | 3 |
| Pentylene glycol | 3 |

-continued

|  | % |
|---|---|
| Glyceryl stearate | 3 |
| PEG-100 stearate | 2.5 |
| Beeswax | 1.5 |
| Dicaprylyl carbonate | 1.5 |
| Cetyl alcohol | 1 |
| Stearyl alcohol | 1 |
| Dimethicone | 1 |
| Phase C | |
| Sodium hydroxide | 0.04 |
| Water | q.s. 100 |

The gelling agents of phase A are dispersed in water then heated to 80-85° C. before dissolving the compounds. The compounds of phase B are heated to 85° C. to form a homogeneous phase. Phase A is emulsified in phase B by means of an. Ystral mixer.

The oil/water emulsion is finally neutralized by means of an aqueous solution of sodium hydroxide, then cooled.

The composition obtained is a moisturizing cream intended to be applied to the face, in particular to areas exhibiting signs of aging or of skin dryness.

3—SPF 50 Sun Protection Cream

| INCI | weight % |
|---|---|
| Peppermint extract | 0.1 |
| Water | q.s. 100 |
| Butyleneglycol dicaprate/dicaprylate | 10.6 |
| Ethylhexyl methoxycinnamate | 7.5 |
| Methylene bis-benzotriazolyl tetramethylbutylphenol | 5 |
| Dicaprylyl carbonate | 4 |
| Butylene glycol | 3.7 |
| Bis-ethylhexyloxyphenol methoxyphenyl triazine | 3 |
| Dimethicone | 2 |
| Caprylyl methicone | 2 |
| VP/Eicosene copolymer | 2 |
| Behenyl alcohol | 2 |

| INCI | weight % |
|---|---|
| Glycerol | 2 |
| Potassium cetyl phosphate | 2 |
| Cetearyl alcohol | 1.2 |
| phenylbenzimidazole sulfonic acid | 1 |
| tromethamine | 1 |
| Phenoxyethanol | 0.9 |

The cream has an SPF value equal to 50. The combination of the peppermint extract with the UV screening agents makes it possible to protect the epidermis from UV radiation and makes it possible to maintain cutaneous cell renewal by keratinocyte progenitor cells.

The invention claimed is:

1. A method for increasing renewal of epidermal cells in a skin suffering from a disordered regenerative process and from a deficient expression of NOTCH protein in keratinocyte progenitor cells, said method comprising applying on at least one portion of the skin an effective amount of a peppermint extract that is obtained by enzymatic hydrolysis of aerial parts of a peppermint plant in an aqueous medium.

2. The method as claimed in claim 1, wherein the NOTCH protein is NOTCH 1 protein or NOTCH 2 protein.

3. The method as claimed in claim 2, wherein gene expression quantification (RQ) of a gene coding for the NOTCH protein is greater than 1, said gene expression quantification being measured by quantitative real-time PCR (qRT-PCR).

4. The method as claimed in claim 1, wherein said extract is applied on skin located on at least one of the face, eye contour, neckline, lips, and hands of a person.

5. The method as claimed in claim 1, comprising applying on the skin an effective amount of an aqueous extract of beech, which is also called *Fagus Sylvatica*, buds or an effective amount of an aqueous extract of *Bellis perennis* flowers.

\* \* \* \* \*